United States Patent [19]

Fujiwara et al.

[11] 4,271,268

[45] Jun. 2, 1981

[54] PROCESS FOR PRODUCING D-ARABITOL

[75] Inventors: Akiko Fujiwara, Kamakura; Setsuko Masuda, Yokohama, both of Japan

[73] Assignee: Hoffmann-La Roche Inc., Nutley, N.J.

[21] Appl. No.: 940,690

[22] Filed: Sep. 8, 1978

[30] Foreign Application Priority Data

Sep. 12, 1977 [LU] Luxembourg .............................. 78114

[51] Int. Cl.$^3$ .............................................. C12P 7/18
[52] U.S. Cl. .................................... 435/158; 435/938
[58] Field of Search ......................... 435/105, 158, 938

[56] References Cited

U.S. PATENT DOCUMENTS

| | | | |
|---|---|---|---|
| 2,986,495 | 5/1961 | Onishi | 435/938 X |
| 3,607,652 | 9/1971 | Ueda | 435/938 X |

FOREIGN PATENT DOCUMENTS

| | | | |
|---|---|---|---|
| 1122 | 3/1979 | European Pat. Off. | 435/158 |
| 19261978 | 2/1970 | Fed. Rep. of Germany . | |
| 822154 | 10/1959 | United Kingdom | 435/158 |

OTHER PUBLICATIONS

Chem. Abs., 59: 3288f (1963).
Chem. Abs., 69: 95094v (1968).
Chem. Abs., 82: 56007f (1975).
Hattori, K. et al. "Microbial Production of D-Arabitol by n-Alkane-Grown *Candida tropicalis*," Agr. Biol. Chem., 38 (10) 1974, pp. 1875–1881.

*Primary Examiner*—Robert A. Yoncoskie
*Attorney, Agent, or Firm*—Jon S. Saxe; Bernard S. Leon; George W. Johnston

[57] ABSTRACT

The preparation of D-arabitol by a fermentative process utilizing a micro-organism of the species *Pichia haplophila* or mutants thereof in a nutrient medium containing as a carbon source a hydrocarbon or ethyl alcohol is disclosed.

14 Claims, No Drawings

PROCESS FOR PRODUCING D-ARABITOL

BACKGROUND OF THE INVENTION

This invention relates to a fermentative process for producing D-arabitol having the empirical formula $C_5H_{12}O_5$.

In fermentation processes for preparing D-arabitol known hitherto, yeasts of the genera Candida, Saccharomyces, Hansenula, Debaryomyces, Torulopsis, Pichia or Endomycopsis are used, and nutrient media containing carbohydrates such as glucose, sucrose or glycerol, as the principal carbon source are employed. These known processes have various disadvantages, however. The substances such as glucose, glycerol and sucrose, employed as nutrient media are expensive. Furthermore, it is very difficult to separate the D-arabitol formed in these processes from the sugars used as the carbon source.

A process is known for preparing D-arabitol by cultivating a yeast of the genus Candida or Torulopsis, in which relatively inexpensive starting materials, such as hydrocarbons or ethyl alcohol, are employed in the nutrient media as the main carbon source (Agricultural and Biological Chemistry, Volume 38, 1875–1888, 1974). This article reports, however, that the yeast *Pichia membranfaciens* in a nutrient medium containing hydrocarbons as the principal carbon source produces no D-arabitol at all. It has also been established experimentally that other micro-organisms of the genus Pichia, for example *P. fluxnum*, *P. fermentans* and *P. toletana*, do not produce any D-arabitol in culture media containing hydrocarbons.

In the present invention, it has surprisingly been found that a specific species of Pichia, namely *Pichia haplophila*, and mutants derived therefrom fermentatively produce D-arabitol in high yields from inexpensive hydrocarbons or ethyl alcohol.

The arabitol thus obtained by the process of the present invention can advantageously be separated in a simple manner from the culture liquor.

SUMMARY OF THE INVENTION

The present invention concerns a fermentative process for producing D-arabitol. The process comprises cultivating a micro-organism of the species *Pichia haplophila* or a mutant thereof in a nutrient medium containing as a carbon source a hydrocarbon or ethyl alcohol or mixtures thereof. The nutrient medium may contain other additives and the cultivation is suitably carried out at temperatures in the range of about 20° to about 40° C. The resulting D-arabitol is useful as a sweetening agent and as an intermediate.

DETAILED DESCRIPTION OF THE INVENTION

The pesent invention relates to a process for producing a sugar alcohol known as D-arabitol by utilizing a micro-organism of the species *Pichia haplophila* or its mutants in a nutrient medium containing a carbon source selected from the group consisting of hydrocarbon and ethyl alcohol. The polyalcohol D-arabitol thus obtained is suitable as a sweetening agent and is also useful as an intermediate in the preparation of various carbohydrates and other compounds.

As used herein, hydrocarbon denotes liquid or solid paraffin, isoparaffin and olefin. Paraffin connotes a straight chain saturated compound having the empirical formula $C_nH_{2n+2}$ wherein n is 10 to 20, preferably 13 to 16. Isoparaffin connotes a branched chain compound having the empirical formula $C_nH_{2n+2}$ wherein n is 10 to 20, preferably 13 to 16. Olefin denotes a straight or branched chain unsaturated compound having the empirical formula $C_nH_{2n}$, wherein n is 10 to 20, preferably 13 to 16. Ethyl alcohol is the alkanol of the formula $C_2H_5OH$.

The D-arabitol-producing micro-organisms used in the process according to the invention are yeasts of the species *Pichia haplophila* that can produce D-arabitol from hydrocarbons or ethyl alcohol and mutants thereof. Such mutants can be obtained from the parent strains by normal mutation methods, for example by irradiation with UV light, X-rays or γ-rays, or by treatment with suitable mutagens.

The strains of *Pichia haplophila* preferably used according to the process of the invention have been deposited with the NRRL and FRI, and are namely the strains *Pichia haplophila* NRRL 11,175 (FERM P-3955) and *Pichia haplophila* NRRL 11,176 (FERM P-3956). The latter strain was obtained from the strain *Pichia haplophila* NRRL 11,175 (FERM P-3955) by irradiation with UV light.

Any conventional nitrogen source may be utilized in accordance with this invention. Peptone, cornsteep liquor, yeast extract, meat extract, ammonium sulphate, ammonium nitrate, urea and the like, either alone or in combination, may be used as the nitrogen source. The nutrient medium may also contain inorganic salts, such as for example calcium carbonate, sodium chloride, sodium phosphate and the like, as well as additives such as vitamins, amino acids and the like.

The process according to the invention is carried out by cultivating the D-arabitol-producing micro-organisms in a liquid medium containing the afore-mentioned carbon sources, nitrogen sources, inorganic salts and, if required, other organic or inorganic nutrients. Liquid or solid paraffins, olefins and isoparaffins with different numbers of carbon atoms, or mixtures thereof, can be used as hydrocarbons. An alternative carbon source is ethyl alcohol.

The concentration of the carbon source depends on the strain of *Pichia haplophila* employed and the culture conditions. Preferred concentrations when using hydrocarbons are in the range from about 3 to about 30% by volume and when using ethyl alcohol between about 1 and 20% by volume, in each case based upon the total volume of the nutrient medium.

Any conventional method of cultivation can be used to affect the disclosed conversion. The cultivation is preferably carried out under aerobic conditions, in particular by means of agitated culture or submersed culture. The optimum cultivation temperature is in the range between about 20° and about 40° C., and the optimum pH is between about 2.0 and 8.0, preferably between about 2.0 and 6.0. The fermentation time is generally between about 3 and 10 days.

D-arabitol can be separated from the fermentation liquor by using methods known per se, for example by means of ion exchange resins or by solvent extraction.

The following Examples are given for the purpose of illustrating the invention. Unless otherwise stated, temperatures are in degrees Celsius (°C.).

The terms "Dowex 50W×4, H+-type" and "Amberlite IR-45, OH−-type" refer to ion exchange resins manufactured by The Dow Chemical Company and Rohm & Has, respectively.

EXAMPLE 1

30 ml of a nutrient medium containing 5% wt./vol. of n-paraffins of the composition: $C_{13}$ 0.3%, $C_{14}$ 50%, $C_{15}$ 49.5% and $C_{16}$ 0.2%, 0.2% wt./vol. ammonium chloride, 0.05% wt./vol. monopotassium phosphate, 0.5% wt./vol. $MgSO_4.7H_2O$, 0.1% wt./vol. yeast extract and 0.5% wt./vol. calcium carbonate are inoculated, in a 500 ml flask, with Pichia haplophila NRRL 11,176 (FERM P-3956). (This strain is the mutant of Pichia haplophila NRRL 11,175 (FERM P-3955) obtained by irradiating the cell suspension with a UV lamp at a distance of 30 cm for 5 minutes.) The fermentation is carried out for 6 days at 30° C. on a rotating agitation device. Approximately 10 mg D-arabitol are obtained per ml of nutrient medium. After removing the cells by centrifugation, the filtrate is passed through a cation exchange resin (Dowex 50W×4, H+-type) and an anion exchange resin (Amberlite IR-45, OH−-type), and the filtrate is evaporated to dryness under reduced pressure. Warm ethyl alcohol is added to the residue and the extract is evaporated to a smaller volume and allowed to stand overnight at 5° C. 170 mg of D-arabitol having a melting point of 102°–103° C. are obtained: $[\alpha]_D^{20} = +13.1$ (c=9.91 in saturated borax solution).

EXAMPLE 2

The procedure is similar to that of Example 1, except that the strain Pichia haplophila NRRL 11,175 (FERM P-3955) is used instead of Pichia haplophila NRRL 11,176. About 4 mg of D-arabitol per ml of nutrient medium are obtained in this case.

When it is attempted to carry out the fermentation with, respectively, Pichia fluxnum IFO-0773, Pichia membranfaciens IFO-0864, Pichia membranfaciens IFO-1004, Pichia fermentans NRRL y-1619 and Pichia toletana IFO-0950, no D-arabitol is obtained.

EXAMPLE 3

30 ml of a nutrient medium (2% wt./vol. ethyl alcohol, 0.2% wt./vol. ammonium chloride, 0.06% wt./vol. $KH_2PO_4$, 0.05% wt./vol. $MgSO_4.7H_2O$, 0.1% wt./vol. yeast extract and 0.5% wt./vol. calcium carbonate) are inoculated with Pichia haplophila NRRL 11,175 (FERM P-3955) in a 500 ml flask and fermented for 6 days at 30° C. while agitating. 6 ml of ethyl alcohol are added to the culture, on each of the 4th and 5the days. 3 mg of D-arabitol are obtained per ml of fermentation solution.

The Pichia haplophila strain NRRL 11,176 (FERM P-3956) used in Example 1 has the following properties: the cells are round to oval and measure approximately 3.0 to 5.1×2.0 to 3.0 μm; they occur individually, in pairs, or in groups. A sediment and a thin, matt, diffuse membrane are formed. The stab culture is white and finely plicated. A primitive pseudomycelium can form. An ascus formation is observed on gypsum blocks. The spores are simicircular.

Fermentation: negative.

Assimilation of carbon-containing compounds:

| Glucose | + | D-ribose | + |
|---|---|---|---|
| Galactose | + | L-rhamnose | − |
| L-sorbose | − | Ethanol | + |
| Sucrose | − | Glycerol | + |
| Maltose | − | Erythritol | + |

-continued

| Cellobiose | − | Ribitol | + |
|---|---|---|---|
| Trehalose | − | Galactitol | + |
| Lactose | − | D-mannitol | + |
| Melibiose | − | D-glucitol | + |
| Raffinose | − | α-Methyl-D-glucoside | − |
| Melecitose | − | Salicinol | − |
| Inulin | − | DL-lactic acid | − |
| Soluble starch | W* | Succinic acid | − |
| D-xylose | + | Citric acid | − |
| L-arabinose | + | Inositol | − |
| D-arabinose | w | | |

*w = only slight assimilation observed

Fission or arbutinol: negative
Assimilation of potassium nitrate: negative
Growth in a vitamin-free medium: negative
Growth on a 50% (wt./wt.) glucose-yeast extract-agar: negative
Growth at 37° C.: negative The above-described properties agree with those of the parent strain Pichia haplophila NRRL 11,175 (FERM P-3955) and also with the description of Pichia haplophila in "The Yeasts: A taxonomic study" by N. J. W. Kreger-Van Rij, pages 492–494, 1970, North-Holland Publishing Company.

We claim:

1. A process for producing D-arabitol comprising cultivating a micro-organism of the species Pichia haplophila or mutants thereof in a nutrient medium containing a carbon source selected from the group consisting of a hydrocarbon and ethyl alcohol.

2. The process of claim 1 wherein the micro-organism is Pichia haplophila NRRL 11,175 or Pichia haplophila NRRL 11,176.

3. The process of claim 1 wherein the hydrocarbon is a paraffin, isoparaffin or olefin.

4. The process of claim 1 wherein the nutrient medium contains a hydrocarbon at about 3% to about 30% by volume of nutrient medium.

5. The process of claim 1 wherein the nutrient medium contains ethyl alcohol at about 1% to about 20% by volume of nutrient medium.

6. The process of claim 1 wherein the cultivation is carried out at a temperature between about 20° C. and about 40° C.

7. The process of claim 1 wherein the cultivation is carried out at a pH of about 2 to about 8.

8. The process of claim 7 wherein the cultivation is carried out at a pH of about 2 to about 6.

9. A process for producing D-arabitol comprising cultivating a micro-organism of the species Pichia haplophila NRRL 11,175 in a nutrient media containing as a carbon source a hydrocarbon at about 3% to about 30% by volume of nutrient medium, said cultivation being carried out at a temperature between about 20° C. and about 40° C. and at a pH of about 2 to about 6.

10. The process of claim 9 wherein the hydrocarbon is a paraffin, isoparaffin or olefin.

11. A process for producing D-arabitol comprising cultivating a micro-organism of the species Pichia haplophila NRRL 11,175 in a nutrient media containing as a carbon source ethyl alcohol at about 1% to about 20% by volume of nutrient medium, said cultivation being carried out at a temperature between about 20° C. and about 40° C. and at a pH of about 2 to about 6.

12. A process for producing D-arabitol comprising cultivating a micro-organism of the species Pichia haplophila NRRL 11,176 in a nutrient media containing as a carbon source a hydrocarbon therein at about 3% to about 30% by volume of nutrient medium, said cultivation being carried out at a temperature between about 20° C. and about 40° C. and at a pH of about 2 to about 6.

13. The process of claim 12 wherein the hydrocarbon is a paraffin, isoparaffin or olefin.

14. A process for producing D-arabitol comprising cultivating a micro-organism of the species *Pichia haplophila* NRRL 11,176 in a nutrient media containing as a carbon source ethyl alcohol at about 1% to about 20% by volume of nutrient medium, said cultivation being carried out at a temperature between about 20° C. and about 40° C. and at a pH of about 2 to about 6.

* * * * *